(12) United States Patent
Tollini

(10) Patent No.: US 6,565,537 B2
(45) Date of Patent: May 20, 2003

(54) TUBE SECURING ASSEMBLY

(76) Inventor: Dennis R. Tollini, 9193 Beech Meadow Ct., Clarence Center, NY (US) 14032

( * ) Notice: Subject to any disclaimer, the term of this patent is extended or adjusted under 35 U.S.C. 154(b) by 0 days.

(21) Appl. No.: 09/837,779

(22) Filed: Apr. 18, 2001

(65) Prior Publication Data

US 2002/0156423 A1 Oct. 24, 2002

(51) Int. Cl.[7] .............................................. A61M 5/32
(52) U.S. Cl. ...................................... 604/174; 604/179
(58) Field of Search ................................ 604/174, 175, 604/178, 179, 180; 128/DIG. 26

(56) References Cited

U.S. PATENT DOCUMENTS

| 3,556,096 | A |   | 1/1971  | Fuller et al. |         |
|-----------|---|---|---------|---------------|---------|
| 3,823,713 | A |   | 7/1974  | Shah          |         |
| 3,834,380 | A |   | 9/1974  | Boyd          |         |
| 3,926,705 | A | * | 12/1975 | Todd          | 156/155 |
| 5,147,322 | A | * | 9/1992  | Bowen et al.  | 604/180 |
| 5,242,430 | A | * | 9/1993  | Arenas et al. | 604/280 |
| 5,266,401 | A |   | 11/1993 | Tollini       |         |
| 5,300,037 | A |   | 4/1994  | Delk et al.   |         |
| 5,520,656 | A |   | 5/1996  | Byrd          |         |

* cited by examiner

Primary Examiner—Brian L. Casler
Assistant Examiner—Ann Y Lam
(74) Attorney, Agent, or Firm—Joseph P. Gastel

(57) ABSTRACT

A tube securing assembly consisting of a base, which is either a tape or a band, a tab attached to the base, and a loop member, which is either a closed loop member, such as an O-ring, or an open loop member, such as a C-shaped member, associated with the tab to secure a tube thereto when an attachment member, such as hook fabric, on the tab is attached to an attachment member, such as pile fabric, on the base.

57 Claims, 13 Drawing Sheets

FIG. 1
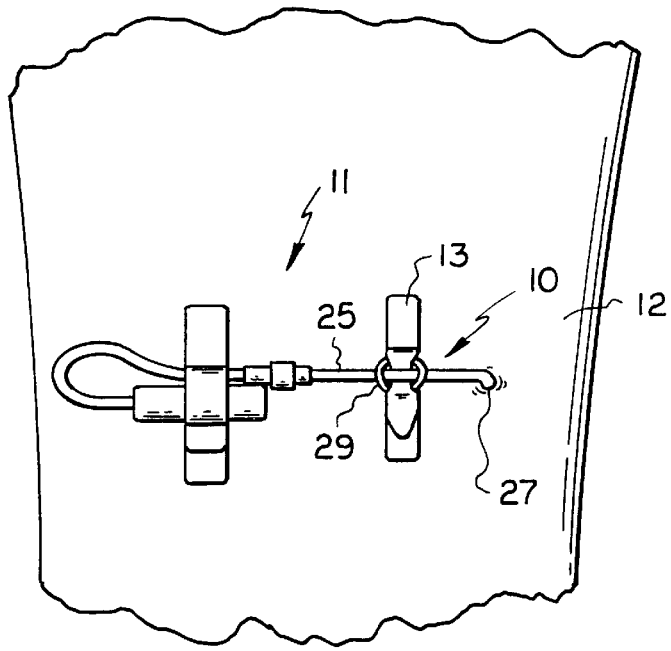
FIG. 2
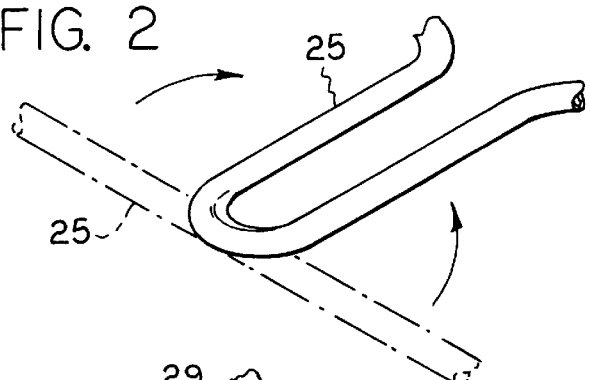
FIG. 3
FIG. 1A
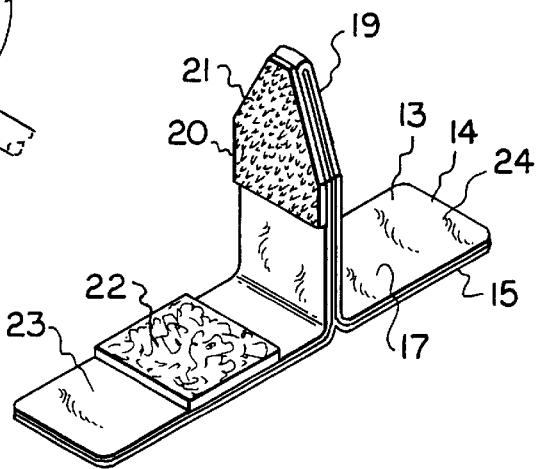

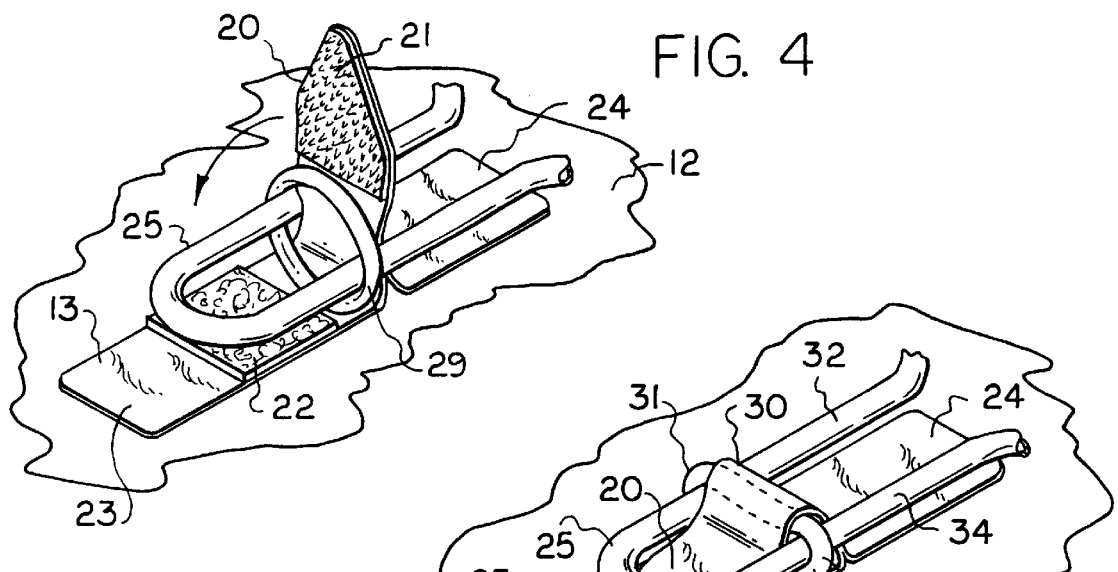
FIG. 4
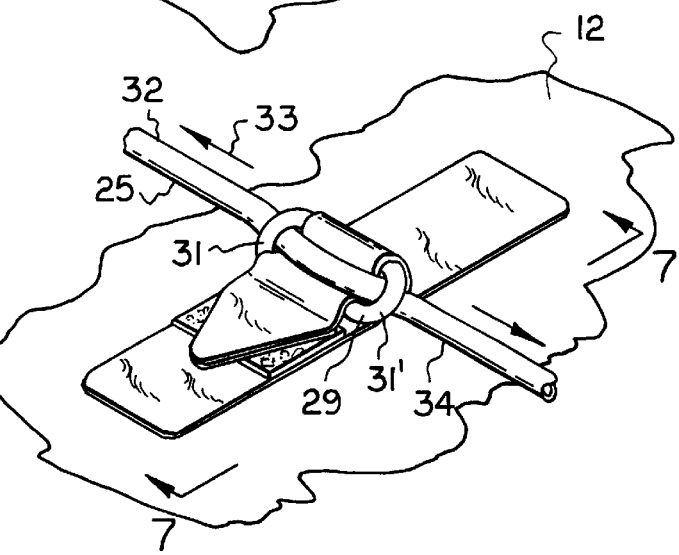
FIG. 5
FIG. 6
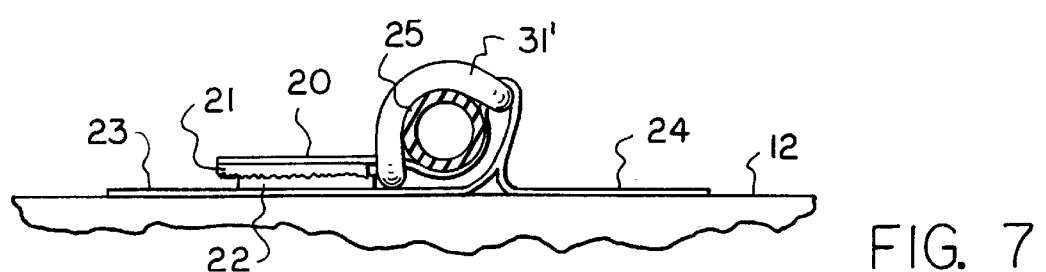
FIG. 7

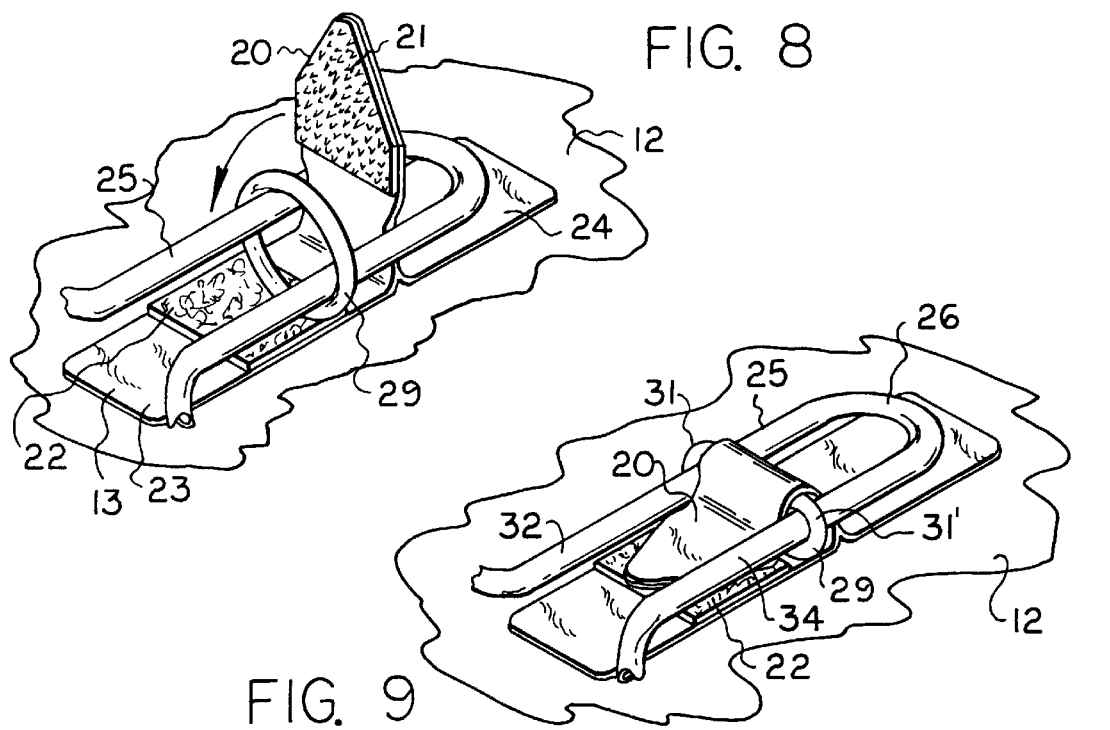
FIG. 8
FIG. 9
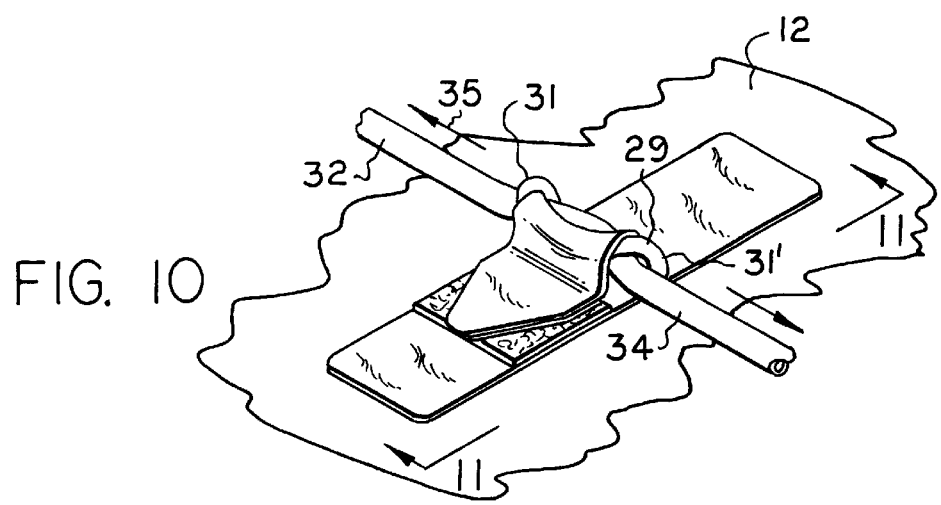
FIG. 10
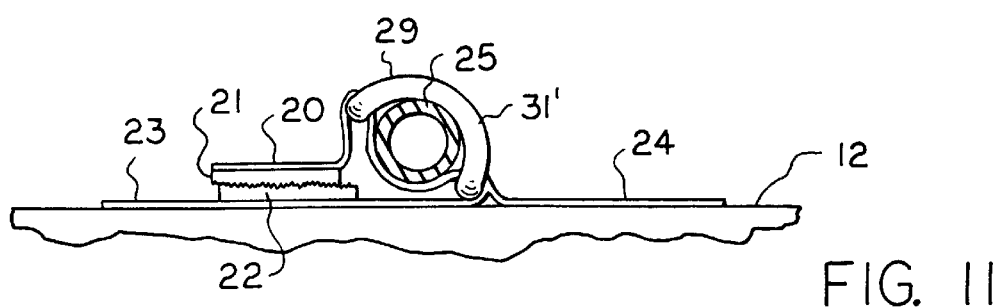
FIG. 11

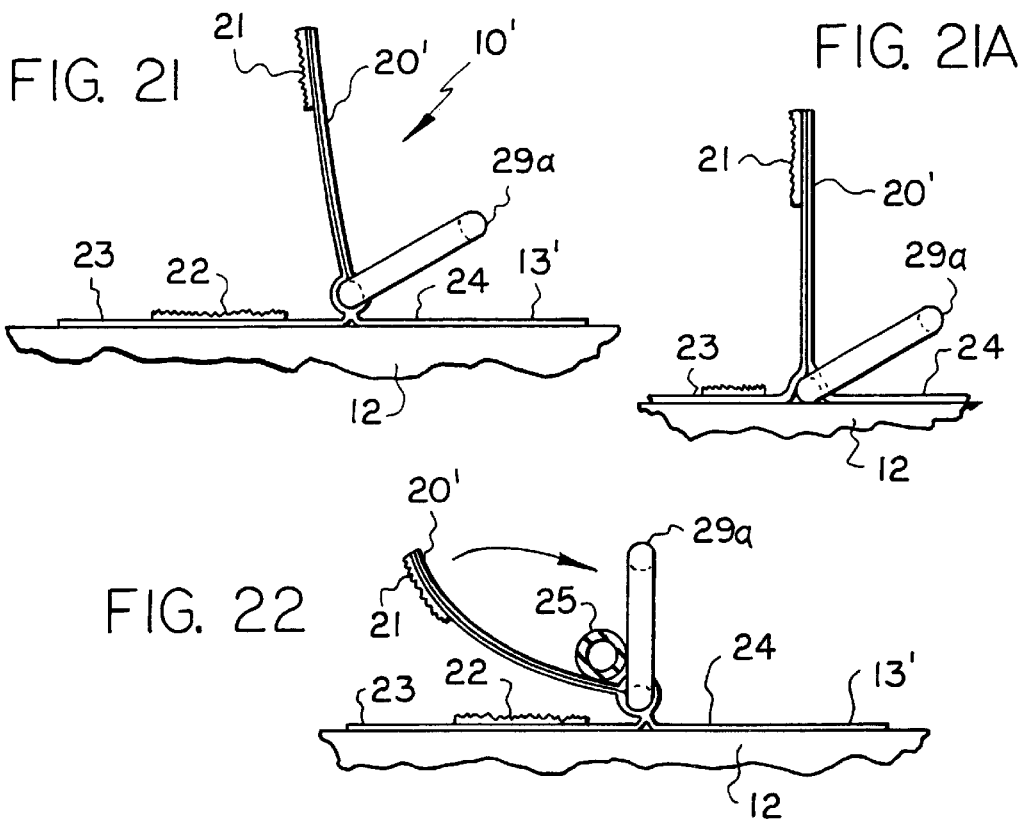
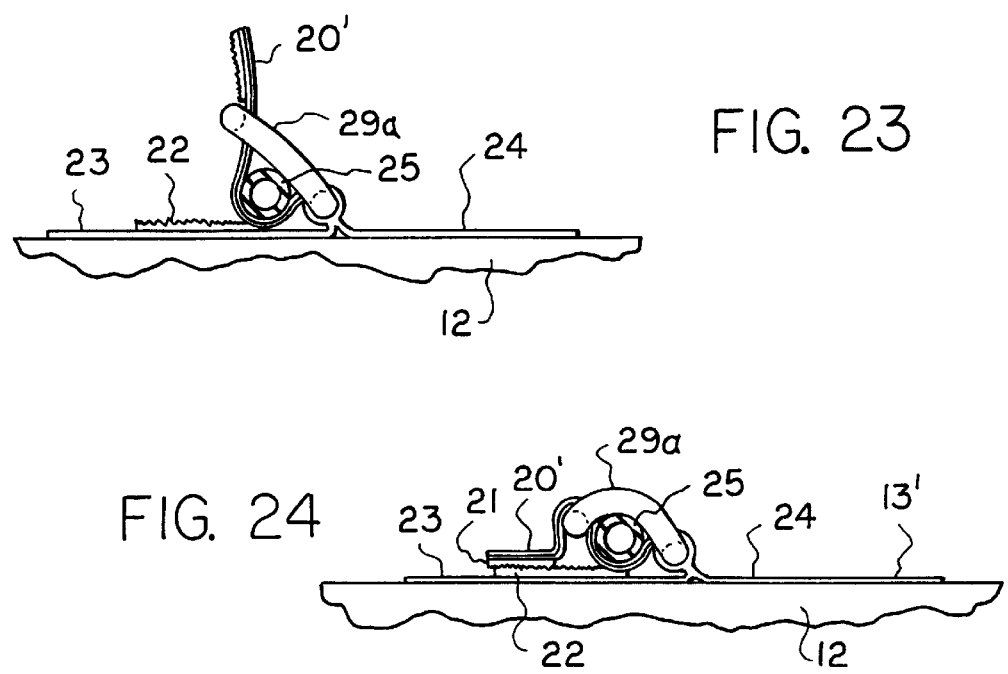

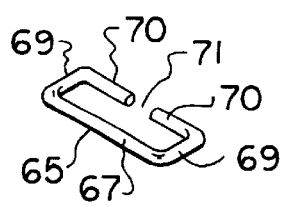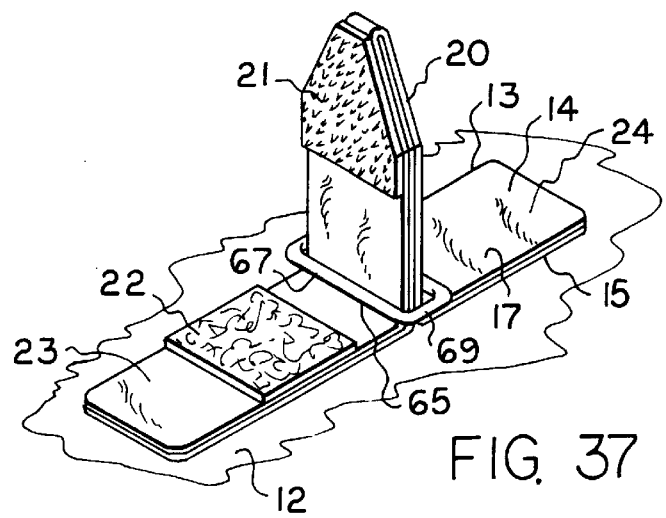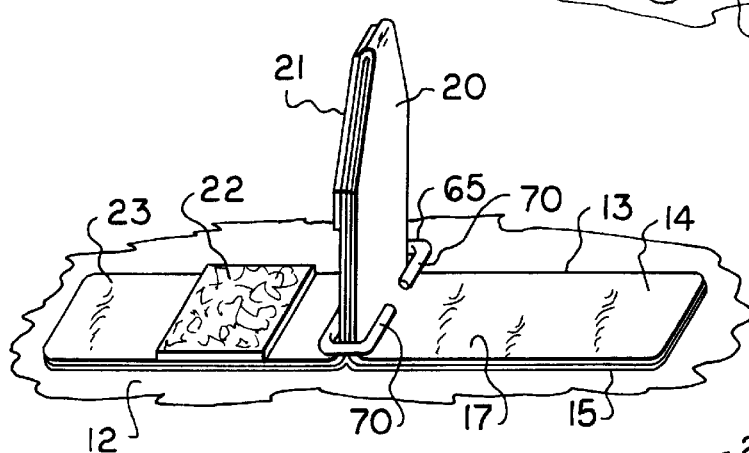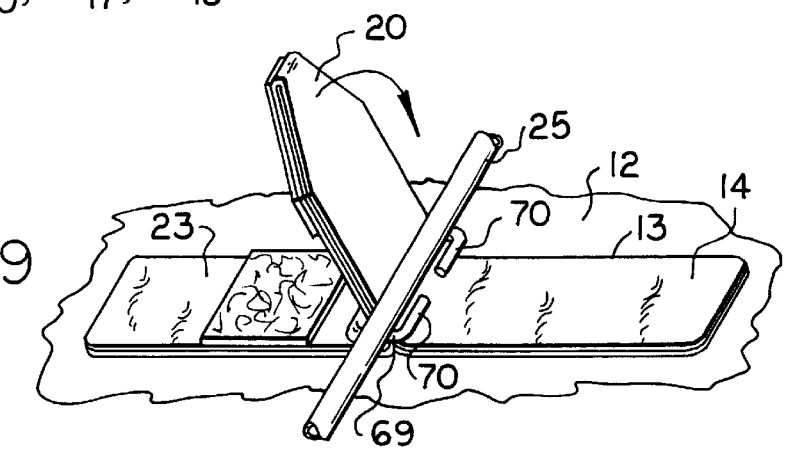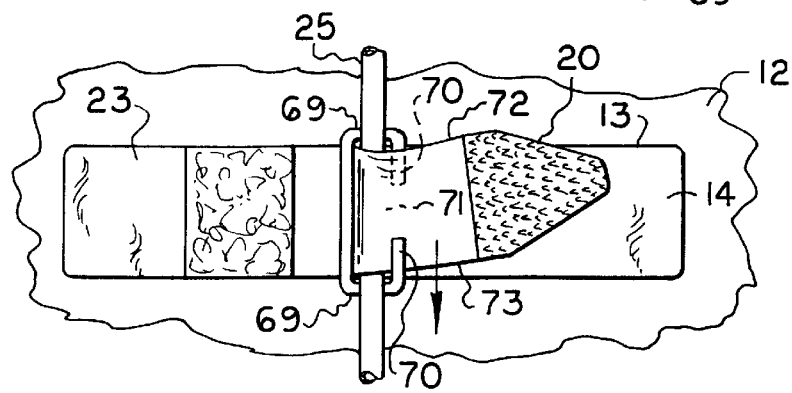

TUBE SECURING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The present invention relates to an improved securing tape assembly for securing a tube to a patient's skin.

By way of background, silicone-type tubing is commonly used in medical applications for conducting fluids to and from a patient's body. In the past, insofar as known, it was difficult to positively secure such tubing in position with a securing tape because the adhesive of the securing tape would not positively adhere to the silicone tubing. In addition, the use of adhesive type of tape in certain circumstances was not desirable because the adhesive could attract unsanitary substances.

BRIEF SUMMARY OF THE INVENTION

It is accordingly one object of the present invention to provide a securing tape assembly having structure which will securely hold silicone tubing and other types of tubing in position on a patient's skin.

Another object of the present invention is to provide a new combination of a tape, a tube and a loop for securing the tube to the tape. Other objects and attendant advantages of the present invention will readily be perceived hereafter.

The present invention relates to a securing assembly comprising a base member, a tab on said base member, and a loop member associated with said tab.

The present invention also relates to a securing tape assembly comprising an elongated tape, first and second surfaces on said elongated tape, pressure-sensitive adhesive on said first surface, a tab extending outwardly relative to said second surface, a first attachment member on said tab, a second attachment member on said second surface, and a loop member positioned relative to said tab.

The present invention also relates to a combination of a securing assembly and a tube comprising a tube, and a securing assembly comprising a base, a tab secured to said base, and a loop member securing said tube to said tab.

The various aspects of the present invention will be more fully understood when the following portions of the specification are read in conjunction with the accompanying drawings wherein:

BRIEF DESCRIPTION OF THE SEVERAL VIEWS OF THE DRAWING

FIG. 1 is a fragmentary plan view of a person's abdomen with the securing tape assembly of the present invention shown holding a catheter which is inserted in the abdomen for peritoneal dialysis;

FIG. 1A is a perspective view of the securing tape portion of the securing tape assembly which comprises the securing tape and an O-ring;

FIG. 2 is a fragmentary perspective view showing the first step of preparing the catheter for attachment to the securing tape assembly by forming it into a U-bend;

FIG. 3 is a fragmentary perspective view of the next step of preparing the catheter by mounting a loop in the form of an O-ring onto the U-bend of the catheter;

FIG. 4 is a fragmentary perspective view showing a securing tape mounted on the abdomen and the O-ring mounted catheter of FIG. 3 positioned on the securing tape;

FIG. 5 is a fragmentary perspective view showing the next step wherein the tab of the securing tape is secured to the base of the securing tape with the O-ring positioned between the tab and the base of the securing tape and the U-bend overlying the tab;

FIG. 6 is a fragmentary perspective view of the next step in the securing of the catheter to the abdomen by pulling on the end of the U-bend to straighten the catheter;

FIG. 7 is a fragmentary cross sectional view taken substantially along line 7—7 of FIG. 6 and showing the catheter secured by the securing tape assembly;

FIG. 8 is a fragmentary perspective view of an alternate way of securing a catheter wherein a securing tape is mounted on the abdomen with the O-ring positioned between the tab and the base of the securing tape, and the tab of the securing tape is positioned proximate the return bend and between the legs of the return bend;

FIG. 9 is a fragmentary perspective view showing the next step of securing the catheter by fastening the tab to the base of the securing tape;

FIG. 10 is a fragmentary perspective view showing the next step in securing the catheter by pulling the catheter into a straightened condition;

FIG. 11 is a fragmentary cross sectional view taken substantially along line 11—11 of FIG. 10;

FIG. 21 is a schematic side elevational view of another type of catheter securing assembly mounted on a base such as the abdomen with the loop secured within the tab;

FIG. 21A is a fragmentary side elevational view showing the loop in the form of a D-ring having a portion captured between the base of the securing tape and a patient's skin at substantially the junction of the portions secured to a patient and below the tab;

FIG. 22 shows the first step in securing a straight catheter to the securing tape by laying it onto the top of the tab;

FIG. 23 shows the next step of securing the catheter to the securing tape by passing the tab through the loop;

FIG. 24 shows the next step of securing the catheter by fastening the tab to the base with the distorted loop engaging the catheter;

FIG. 36 is a perspective view of a loop member having an open side which can be used with the securing tape to hold a catheter relative to a surface;

FIG. 37 is a perspective view of a catheter securing assembly consisting of a securing tape and the loop member mounted on the tab and showing the position of one side of the loop member relative to the tab;

FIG. 38 is a view similar to FIG. 37 but showing the other side of the loop member relative to the tab;

FIG. 39 is a fragmentary perspective view of the securing tape mounted on a surface and showing the first stage of securing a catheter thereto;

FIG. 40 is a fragmentary plan view of the assembly of FIG. 39 showing the next step of securing the catheter to the securing tape assembly;

DETAILED DESCRIPTION OF THE INVENTION

Figure 12:
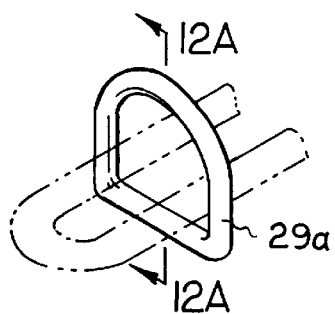
FIG. 12 is a perspective view showing a D-ring which can be used instead of the O-ring of FIGS. 1–11.
Figure 12A:
FIG. 12A is a cross sectional view taken substantially along line 12A—12A of FIG. 12.

Summarizing briefly in advance, the improved catheter securing assembly 10 of the present invention is part of a unit 11 which in this instance is being utilized for peritoneal dialysis through the abdomen 12 of a patient. It will be appreciated, however, that the catheter securing assembly 10 may be used by itself in other applications such as hemodialysis or with the use of other tubes or catheters for infusion or withdrawal of fluids relative to a person's body. In the various dialysis applications it is desirable to avoid the use of adhesive on the catheter because the adhesive allows infection to migrate toward the exit site in the patient's body. Also, adhesive will not firmly hold a silicone type catheter against undesirable movement. The catheter securing assembly of the present invention eliminates undesirable movement of the catheter.

The catheter securing assembly 10 of FIG. 1 includes a securing tape 13 (FIG. 1A) which, in this instance, is an elongated tape 14 which is fabricated from a single piece of tape having a pressure-sensitive adhesive surface 15 and a nonadhesive outer surface 17. The securing tape 13 is formed by bending the central portion 19 on itself so that the adhesive surfaces adhere to each other to form a tab 20. An attachment member in the form of male hook fabric 21 is suitably secured, as by adhesive, to the outer end of tab 20, and an attachment member in the form of pile fabric 22 is secured as by adhesive to end portion 23 of the securing tape. The opposite end portion 24 does not contain any added subject matter. The end portions 23 and 24 constitute the base of the securing tape 13. The securing tape of the type which is used is generally shown in U.S. Pat. Nos. 4,976,700 and 5,098,399 which are incorporated herein by reference. It will be appreciated that any type of a securing tape which has a tab, such as 20, which extends upwardly away from a base which can be secured to a person's body, can be used insofar as it is not inconsistent with the additional structure of the catheter securing assembly which is described hereafter. It is also to be noted that while the structure of the securing tape has been described above relative to FIG. 1A, most of the ensuing drawings show the securing tape in mostly schematic form in that the adhesive layer 15 is not depicted therein, but it will be understood that every securing tape which is shown does have at least pressure-sensitive adhesive on the two end portions 23 and 24 unless the catheter securing assembly is of a type which is not adhesively secured to a person's body.

The securing tape assembly of FIGS. 4–7 is mounted on the abdomen 12 in the following manner. First of all, a securing tape 13 is adhesively secured to the abdomen 12 approximately 3 inches from the entry site 27, which is an opening in the abdomen. Thereafter, the catheter 25 is formed into a U-bend (FIG. 2) by bending it from its dotted line position to its solid line position. Thereafter, a closed loop member in the form of an O-ring 29 is slipped over the U-bend (FIG. 3). The assembled U-bend 25 and O-ring 29 is positioned as shown in FIG. 4 with the O-ring proximate the tab 20 and the U-bend portion 26 located essentially proximate the pile fabric 22. Thereafter, the tab 20 is pulled taut and the hook fabric 21 is placed into mating engagement with the pile fabric 22 with the portion 30 of the tab actually compressing the O-ring 29 into a generally oval shape with its ends 31 and 31' pressing against catheter 25. Thereafter, the leg 32 of the U-bend is pulled in the direction of arrow 33 while the leg 34 of the U-bend is held stationary so that there is no relative movement between the catheter and the entry site 27. The tab 20 thus effectively presses against tube 25. The only relative movement between the catheter 25 and the O-ring 29 is when the catheter leg 32 moves through O-ring portion 31. It does not move relative to O-ring portion 31'. When U-bend leg 32 is moved in the direction of arrow 33, a catheter 25 will straighten from its U-bend orientation of FIG. 5 to a substantially straightened orientation of FIG. 6.

It is to be noted that O-ring 29 is fabricated of a silicone rubber material which is the same material from which catheter 25 is fabricated. The fact that silicone rubber ends 31 and 31' press against the silicone rubber catheter 25 firmly holds the catheter 25 from movement once it has been fully installed as shown in FIGS. 6 and 7. In this respect, it is a characteristic of silicone rubber that two parts of silicone rubber will not slide relative to each other whereas a piece of silicone rubber will generally slide relative to other materials with which it is in engagement unless the engagement is so tight that there is no sliding.

In FIGS. 8–11 another arrangement for mounting a catheter 25 is shown. The securing tape 13 is identical to securing tape 13 of the preceding figures, and identical numerals of prior figures designate identical elements of structure. Therefore, in the interest of brevity this structure will not be described at this point. A comparison of FIGS. 4 and 8 shows how FIG. 8 differs from FIG. 4. In this respect, while the closed end 26 of the return bend of the catheter has been shown proximate the pile fabric in FIG. 4, in FIG. 8, the return bend 26 of the catheter is shown on the opposite side of tab 20 from the pile fabric 22. Thus, the tab 20 can be secured to the pile fabric 22 by moving it between the legs 32 and 34 of the U-bend rather than threading it through the portions of U-bend legs 32 and 34 proximate the closed end 26 of the return bend. Once the parts have been placed in the position of FIG. 9, the leg 32 of the U-bend is pulled in the direction of arrow 35 while leg 34 is held against slipping through portion 31' of O-ring 29. In the position of FIG. 10, loop portions 29 and 31 press against one side of tube 25, and the tab presses on the opposite side of tube 25.

Figure 13:
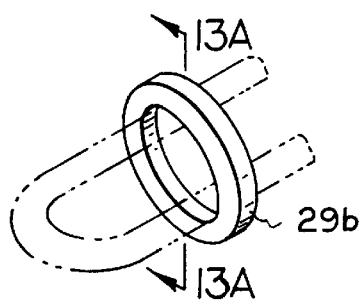
FIG. 13 is a perspective view of another type of O-ring having planar surfaces and sharp edges.
Figure 13A:
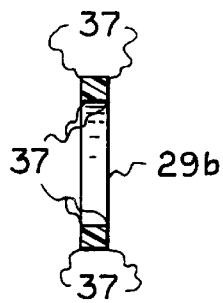
FIG. 13A is a cross sectional view taken substantially along line 13A—13A of FIG. 13.
Figure 13B:
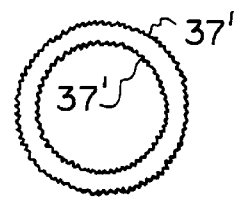
FIG. 13B is a plan view of an O-ring such as shown in FIG. 13 but having serrated edges for providing greater gripping areas.

While O-ring or loop 25 of FIGS. 1–11 has been depicted in the shape of a conventional O-ring having a circular cross section, FIGS. 12–15B depict other closed loop shapes which can be used. In FIG. 12 the loop 29a is in the shape of a D-ring having a circular cross section. In FIG. 13 the loop 29b is in the shape of an O-ring having a square cross section with four sharp edges 37. These sharp edges provide added gripping against slippage. In FIG. 13B the loop 29b is shown as having been further modified by having jagged edges 37' at the four corners of each square cross section for the purpose of providing added gripping.

Figure 14:
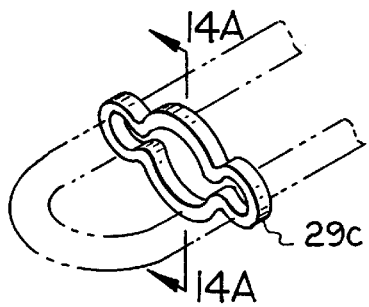
FIG. 14 is a perspective view of a configured O-ring of the shape shown which can be used instead of any other type of O-ring.
Figure 14A:
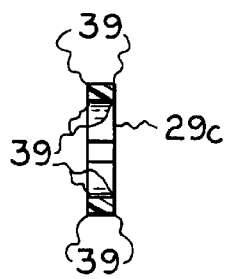
FIG. 14A is a cross sectional view taken substantially along line 14A—14A of FIG. 14.
Figure 14B:
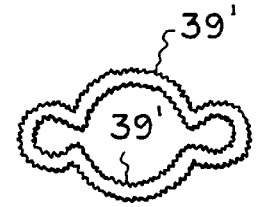
FIG. 14B is a plan view of the loop configuration of FIG. 14 having serrated edges.

In FIG. 14 a still further form of loop 29c is shown which has an undulating outer surface and a square cross section with sharp edges. In FIG. 14B the structure of loop 29c is shown with the jagged edges 37' at the four corners of the square cross section to provide added gripping.

Figure 15:
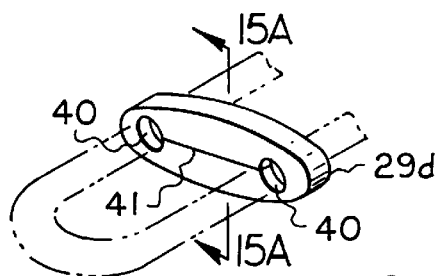
FIG. 15 is a perspective view of another loop configuration which can be used in the securing tape assembly.
Figure 15A:
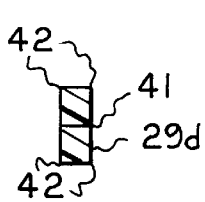
FIG. 15A is a cross sectional view taken substantially along line 15A—15A of FIG. 15.
Figure 15B:
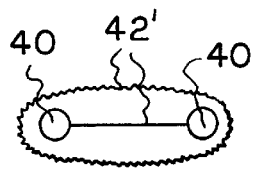
FIG. 15B is a plan view of the loop of FIG. 15 but having serrated edges.
Figure 16:
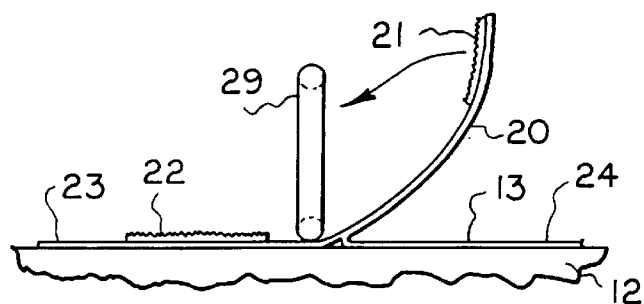
FIG. 16 is a schematic side elevational view showing the first step in attaching a catheter to a surface without forming a U-bend therein by positioning a loop in the form of an O-ring next to the tab of a securing tape secured to a surface such as the abdomen.

In FIG. 15 another form of loop 29d is shown which has a body with two openings 40 therein and a slit 41 separating the openings. The edges 42 are straight lines as described above relative to the edges of the embodiments shown in FIGS. 13A and 14A. In FIG. 15B another embodiment is shown which has jagged edges 42' and 41' where the edges occur. All of the embodiments of FIGS. 12–15, and FIGS. 12A–15A and FIGS. 13B–15B are fabricated out of silicone rubber so that there will be good nonslipping engagement with a silicone rubber tube 25 as described above relative to FIGS. 1–11.

Figure 17:
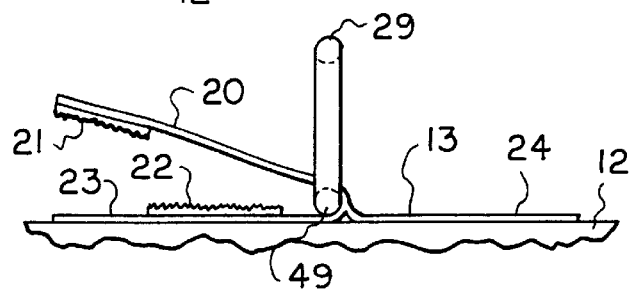
FIG. 17 shows the next step which is passing the securing tape tab through the loop.
Figure 18:
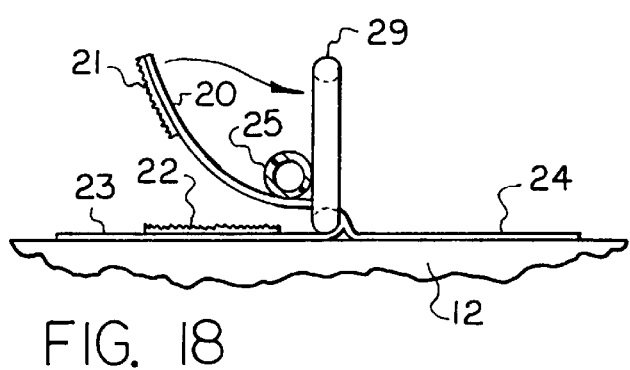
FIG. 18 shows the next step by laying the straight catheter on top of the tab.
Figure 19:
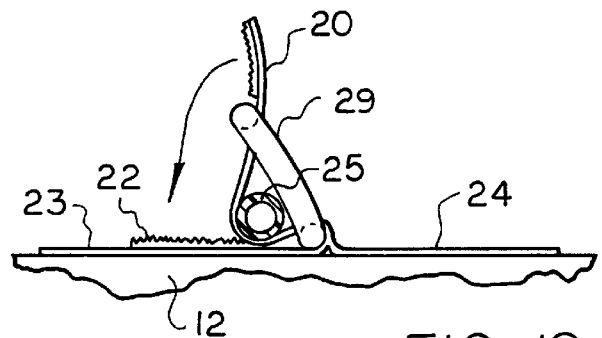
FIG. 19 shows the next step wherein the tab is passed through the loop.
Figure 20:
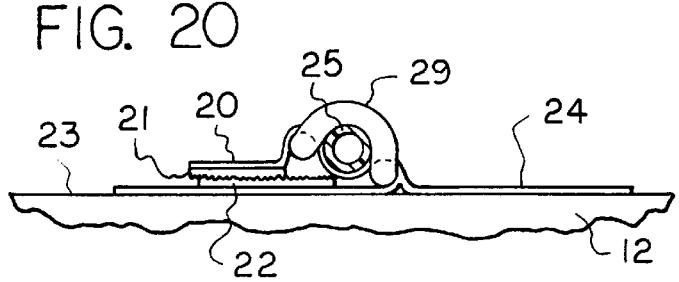
FIG. 20 shows the last step wherein the tab is attached to the base of the securing tape after having distorted the loop into gripping engagement with the catheter.

In FIGS. 1–11 the catheter securing assembly consisting of the securing tape 13 and the O-ring 25 were assembled with the catheter 25 by initially forming the catheter 25 into a U-bend. However, in FIGS. 16–20 a method of assembling the catheter securing assembly with the catheter is effected without forming the U-bend. In FIGS. 16–20 all parts which bear numerals identical to those of FIGS. 1–11 represent identical elements of structure. The catheter securing assembly is secured to the catheter 25 in the following manner. The O-ring 29, without distortion, is oriented between tab 20 and pile fabric 22. Thereafter, the tab 20 is inserted through O-ring 29 (FIG. 17). Thereafter, as shown in FIG. 18, the straight catheter 25 is laid on top of tab 20 and bears against O-ring 29. Then, as shown in FIG. 19, the tab 20 is threaded through O-ring 29 and is pulled taut so as to distort the O-ring 29 into the shape shown in FIG. 20 after the tab 20 has had its hook fabric 21 engaged with the pile fabric 22 on securing tape end 23. The configuration of the assembled parts of FIG. 20 will be the same as that shown in FIG. 6 notwithstanding that a U-bend was not formed into 25 during its securement with the catheter securing assembly.

In FIGS. 21–24 a further embodiment of the present invention is disclosed. In this embodiment, the loop 29a is in the form of a silicone rubber D-ring, such as shown in FIG. 12, and is captured in tab 20' which corresponds to tab 20 of the preceding figures. The remaining portions of the securing tape 13' are identical to the corresponding portions of securing tape 13 and they bear the same numerals. The tab 20', as can be seen from FIG. 1A, is formed of two sides of the elongated tape which are placed with their adhering surfaces in face-to-face relationship and adhered to each other. A portion of the D-ring 29a (FIG. 12) is captured between these two sides, as depicted in FIG. 21. Thus, the catheter securing assembly 10' consists of a securing tape 13' having a D-ring or loop 29a formed integrally therewith. In order to secure the catheter 25 to the tape 13', the catheter 25 in a straightened condition is oriented relative to the tab 20' and D-ring 29a as shown in FIG. 22, that is, it is placed between the upper side of tab 20' and the adjacent side of D-ring 29a. Thereafter, the tab 20' is passed through the D-ring 29a and pulled taut and thereafter the tab 20' is secured to pile fabric 22 by pressing the hook fabric 21 into it. The final assembly of FIG. 24 will appear in perspective substantially the same as depicted in FIG. 10. Instead of capturing D-ring 29a in tab 20', as shown in FIGS. 21–24, the straight portion of the D-ring can be placed below tab 20', substantially at the junction of tape portions 23 and 24, that is, below the tape with the curved portion of the D-ring alongside tab 20', as shown in FIG. 21a. Also, if desired, an O-ring can be substituted for the D-ring.

In FIGS. 25, 25A and 26–28 another embodiment of the present invention is disclosed. This embodiment utilizes a securing tape 13a (FIG. 25A) which is a modification of the securing tape 13 of FIG. 1A. All parts of securing tape 13a which bear numerals which are identical to those of FIG. 1A represent identical elements of structure and therefore will not be described hereafter in the interest of brevity. Securing tape 13a differs from securing tape 13 in that it has a window 44 therein which was cut in one side of tab 20a to expose the adhesive 45 on the other side of the tab. Structure of this type is fully disclosed in U.S. Pat. No. 4,976,600 which has been incorporated herein by reference. Briefly, the window 44 is formed in the side of the tab by cutting it out before the two sides of the tab are adhered to each other, thereby exposing the adhesive 45 which exists on the tape forming the rear side of tab 20a.

Figure 25:
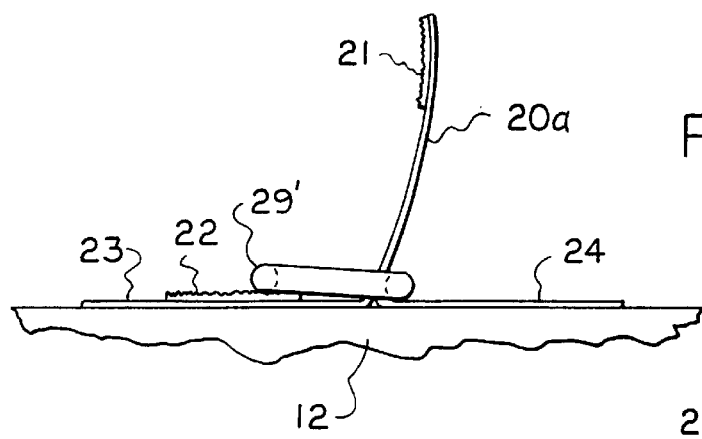
FIG. 25 is a fragmentary side elevational schematic view similar to FIG. 16 but showing a first step of a different way of attaching a catheter to a surface without forming a U-bend therein while still positioning an O-ring next to a securing tape mounted on a surface such as the abdomen.
Figure 28:
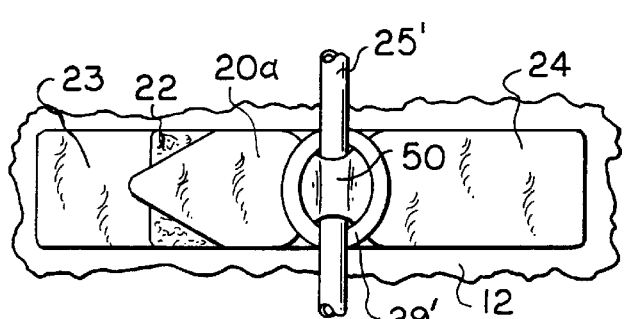
FIG. 28 is a fragmentary plan view of the catheter in completely installed position on a surface such as the abdomen.
Figure 25A:
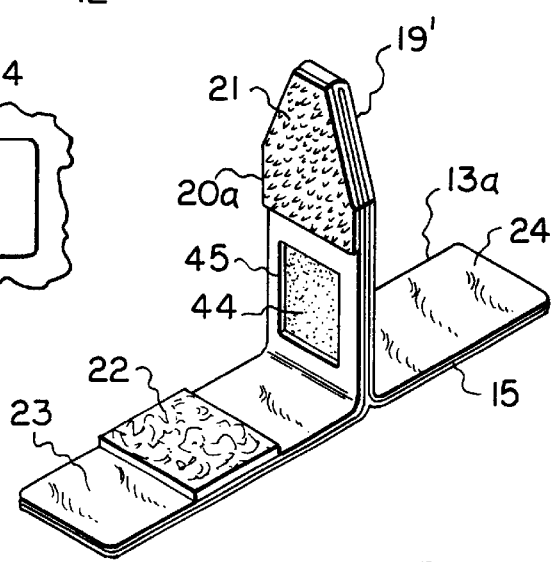
FIG. 25A is a perspective view of the securing tape which is used with the securing tape assembly of FIGS. 25–29.

A securing tape 13a of FIG. 25A can be used with catheters which are not made out of silicone rubber. In this respect, adhesive will hold polyurethane and therefore the adhesive 45 in window 44 will adhere to a tube 25' (FIG. 26) which is fabricated of polyurethane. Therefore, the loop or O-ring 29' need not be fabricated of silicone rubber, but may be fabricated of any desirable rubber compound which is cheaper than silicone rubber. Therefore, an arrangement, such as shown in FIGS. 25–28, may be utilized where adhesive contact with the catheter can be tolerated. In FIG. 28 the tab is shown having concave portions within O-ring 29'. These portions are actually straight, as shown in FIG. 25A, but are formed to concave shapes because they are restricted by the O-ring. However, if desired, the sides of the tab can actually be fabricated with concave configurations on opposite edges, as they appear in FIG. 28.

Figure 26:
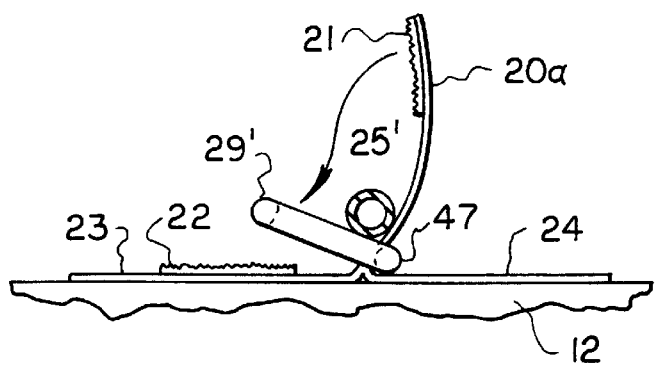
FIG. 26 shows the next step wherein the catheter is placed on the O-ring and against the tab of the securing tape.
Figure 27:
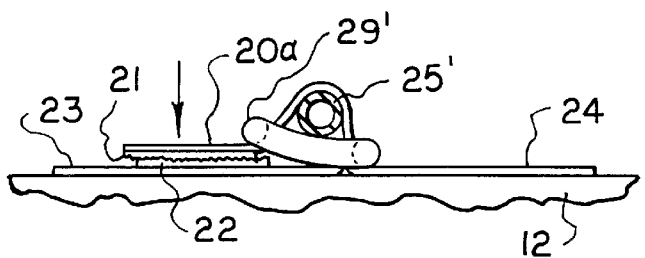
FIG. 27 shows the next step wherein the tab is laid over the catheter and threaded through the O-ring.

The catheter 25', which is of a material other than silicone rubber, is secured to the catheter securing assembly in the following manner. The O-ring or loop 29' is oriented over the tab 20a, as shown in FIG. 26, that is, with the tab 20a being inserted through the loop 29' with the inside of the loop bearing against the side of tab 20a adjacent to end 24. In other words, the portion 47 of loop 29' lies between tab 20a and tape end 24. This is in contrast to the orientation of portion 49 of loop 29 of FIG. 17 wherein it lies between tab 20 and tape end 23. Significance of the foregoing will be appreciated hereafter. The next step is to thread tab 20a through loop 29', as depicted in FIG. 26, and thereafter pull the tab 20a taut and attach its hook fabric 21 to the pile fabric 22 on tape end 23. This will cause the portion 50 of tab 20a to overlie catheter 25 (FIGS. 27 and 28) with the loop 29' having its major portion lying above tab 20a. This causes the adhesive 45 to engage catheter 25. A comparison of FIGS. 28 and 19 clearly demonstrates that when O-ring 29' is oriented relative to the securing tape, as shown in FIG. 26, the tab 20a will overlie the catheter 25 whereas when the loop 29 is oriented as in FIGS. 18 and 19, the catheter 25 will overlie the tab.

Figure 29:
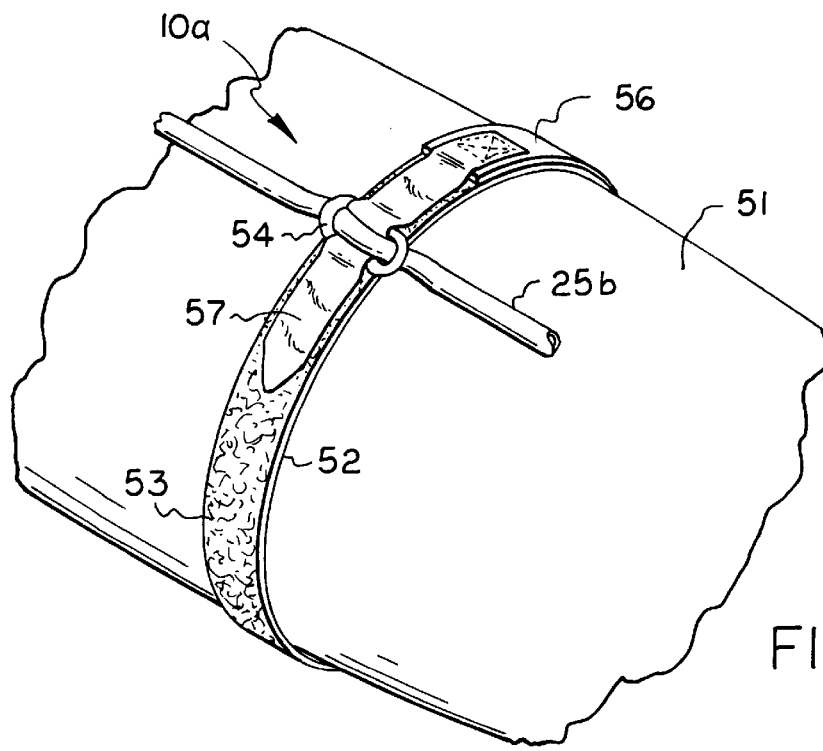
FIG. 29 is a fragmentary perspective view of one embodiment of a catheter secured to a body part such as the arm or leg by a band rather than the securing tape of the preceding figures.
Figure 30:
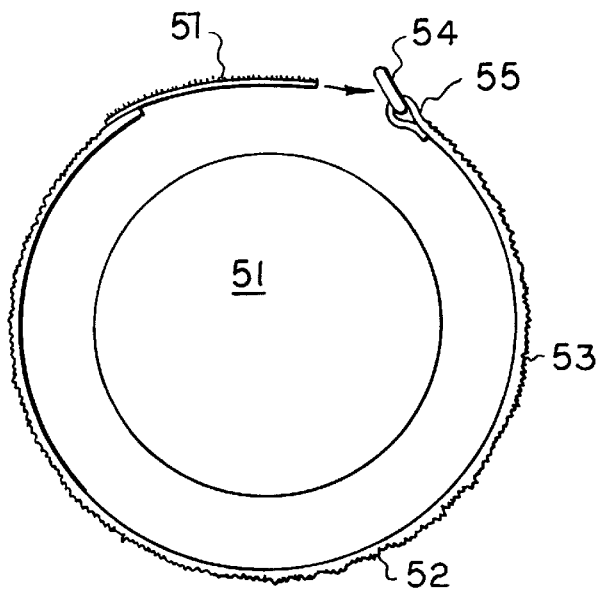
FIG. 30 is a schematic view showing the first step of mounting another embodiment of a band about the arm or leg.
Figure 31:
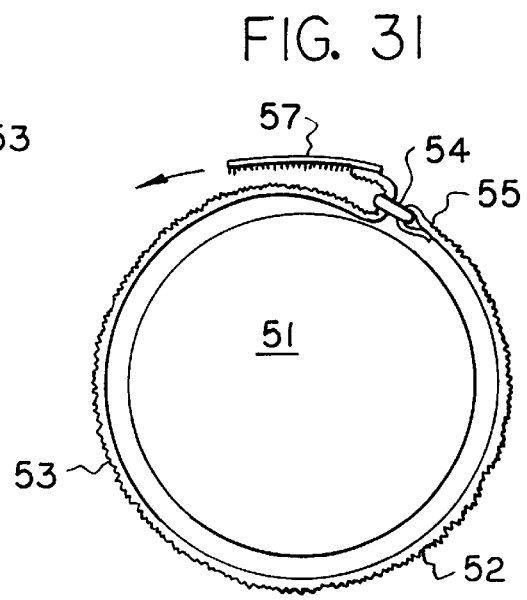
FIG. 31 is a schematic view showing the next step of tightening the band about the arm or leg.
Figure 32:
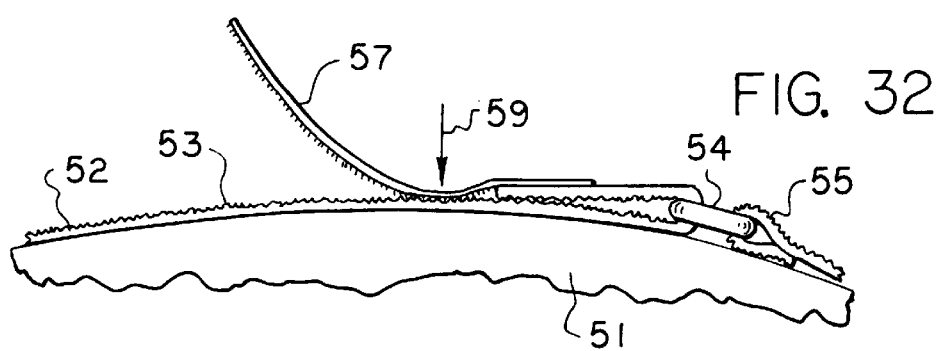
FIG. 32 is a schematic fragmentary enlarged side elevational view showing the next step of the tab being secured to the base of the band.
Figure 33:
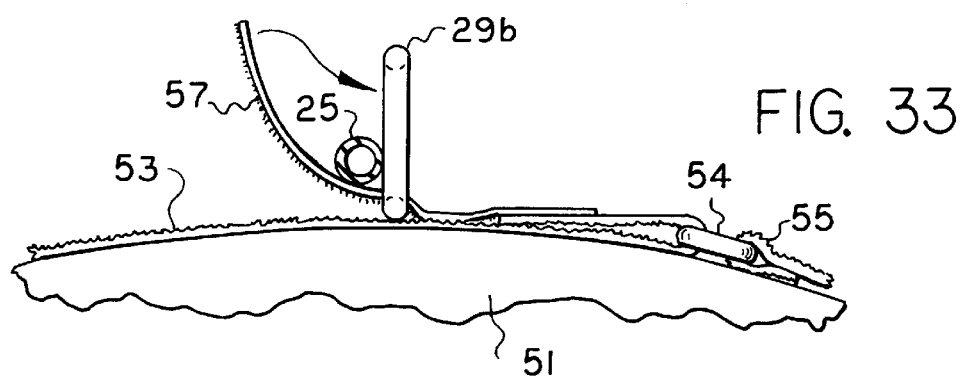
FIG. 33 shows the next step of inserting the tab through a loop such as an O-ring and laying a straight catheter onto the top of the tab.
Figure 34:
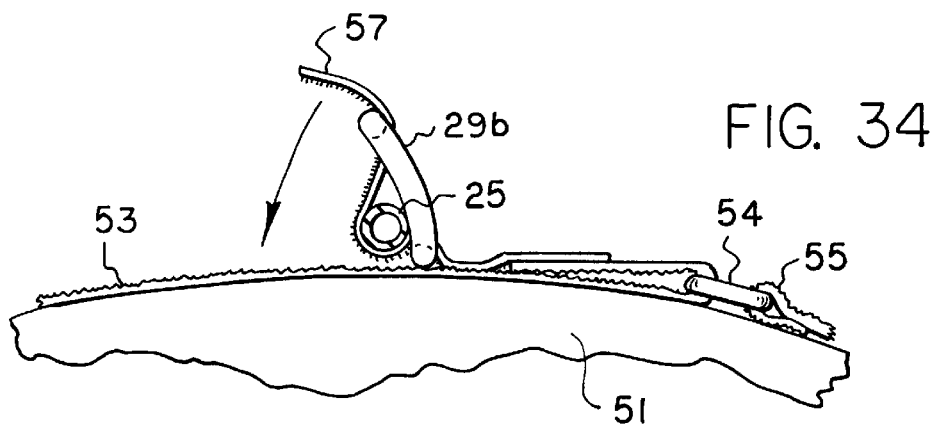
FIG. 34 shows the next step of threading the tab through the loop with the catheter therebetween.
Figure 35:
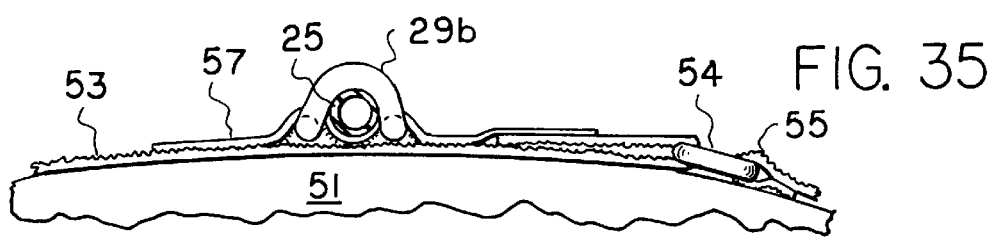
FIG. 35 shows the next step of attaching the tab to the band with the catheter held between the top of the tab and the distorted loop.

In FIGS. 29–35 other embodiments of the present invention are disclosed wherein a catheter 25b is secured to a limb 51, such as an arm or leg, by a base in the form of a band 52 rather than by a securing tape, as depicted in the previous figures. The band 52 has an outer surface 53 of pile fabric. In the embodiment of FIG. 29, the underside of band end 56 can have hook fabric thereon to attach to pile fabric on the top side at the other end of band 52, and the tab 57 will function as described hereafter relative to FIGS. 30–35. In the embodiment of FIGS. 30–35, a loop 54 in the form of an O-ring or a D-ring is secured to the end of band 53 as by a loop 54 formed at the end of band 52. A length of hook fabric 57 is secured to the opposite end of band 52. The band 52 is a base in the sense that it attaches the hook fabric 57 to the body, and the hook fabric 57 is a tab in the sense that it extends outwardly from the base and functions in the same manner as the tabs of the preceding figures.

In the embodiment of FIGS. 30–35, the catheter is secured to the limb 51 in the following manner. First of all (FIG. 32), the hook fabric end or tab 57 is threaded through loop 54 and the band 52 is drawn tight about limb 51, and the attachment member in the form of hook fabric is pressed in the direction of arrow 59 into engagement with the attachment member in the form of pile fabric. A loop 29b, which may be an O-ring or any other configuration of a loop, is then positioned as shown, and the tab 57 is threaded through loop 29b (FIG. 33), and the straight catheter 25 is oriented as shown. Thereafter, the tab 57 is threaded through loop 29b and pressed into the pile fabric 53 (FIG. 35) after it has been pulled taut to distort the loop 29b to the position shown in FIG. 35. The final assembly is depicted in perspective in FIG. 29. The orientation between the tab 57, the loop 29b and the catheter 25b of FIG. 29 is the same as the orientation among the corresponding parts in FIG. 10. However, if an orientation such as shown in FIG. 28 with the tab overlying the catheter is desired, the parts can be oriented as shown in FIGS. 25 and 26 prior to securing the tab 57 to the pile fabric 53. Also, while the tab 57 is shown as being mounted at the end of band 52, it will be appreciated that it can be secured to a central portion of band 52 and that the ends of band 52 can be secured to each other in any suitable manner. While a closed loop member has been shown relative to FIGS. 29–35, it will be appreciated that an open loop member, such as 65 of FIG. 36, can also be used with the embodiments of FIGS. 29–35.

In FIGS. 36–42 another embodiment of a securing tape assembly is shown. The securing tape itself is identical to the securing tape 13 of FIG. 1A and therefore the same numerals which were applied to FIG. 1A are being applied to the securing tape 13 of FIG. 37. An open loop member 65 is positioned over tab 19 as shown in FIGS. 37 and 38. Open loop member 65 is essentially in the form of a C having an elongated side 67, loop portions 69, ends 70 and an opening 71 between loop ends 70. The loop member 65 can be mounted as shown in FIGS. 37 and 38.

Figure 41:
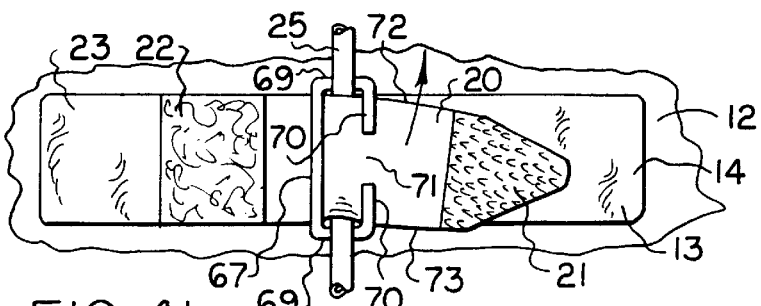
FIG. 41 is a fragmentary plan view similar to FIG. 40 but showing the following step of securing the catheter to the securing tape assembly.
Figure 42:
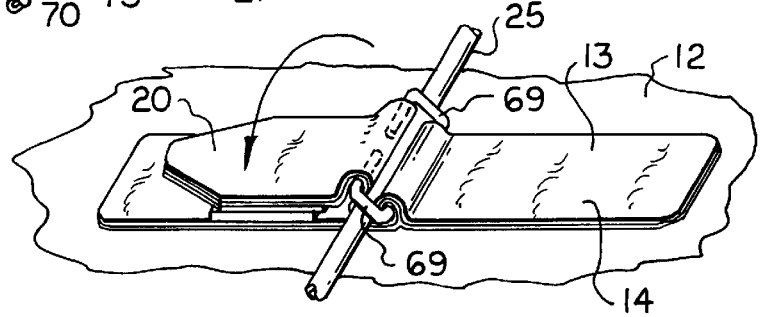
FIG. 42 is a fragmentary perspective view showing the next step of securing a catheter to a securing tape assembly.

In order to secure a catheter 25 to the securing tape assembly of FIGS. 37 and 38, the catheter 25 is laid across loop portions 69 as shown in FIG. 39. Thereafter, the tab 20 is moved in the direction of the arrow (FIG. 39) and passed over the catheter 25, as shown in FIG. 40. The edge 73 of tab 20 is then passed through opening 71 between loop ends 70 and passed underneath loop end 70. Thereafter, as shown in FIG. 41, the edge 72 of tab 20 is passed through opening 71 between loop ends 70 so that it occupies the position shown in FIG. 41 under loop portion 70. Thereafter, tab 20 is pulled taut and moved in the direction of the arrow (FIG. 42) and the male hook fabric 21 is secured to the pile fabric 22 so that the loop portions 69 of the loop member press on one side of catheter 25 and the tab itself presses on the opposite side of catheter 25 to thereby secure the catheter 25 firmly in position.

Figure 43:
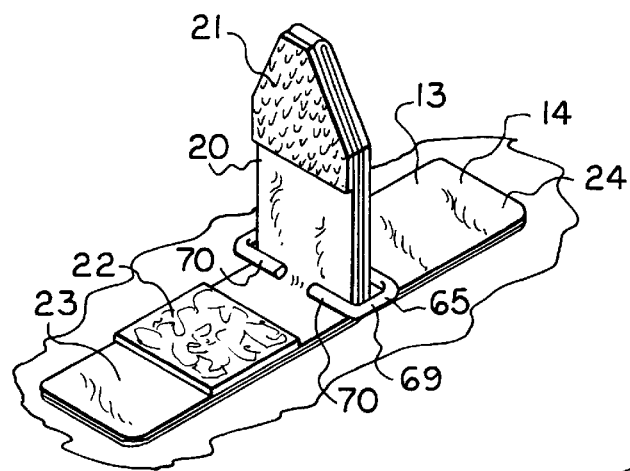
FIG. 43 is a fragmentary perspective view similar to FIG. 37 but showing the loop member in a position which is reverse to that of FIG. 37.
Figure 44:
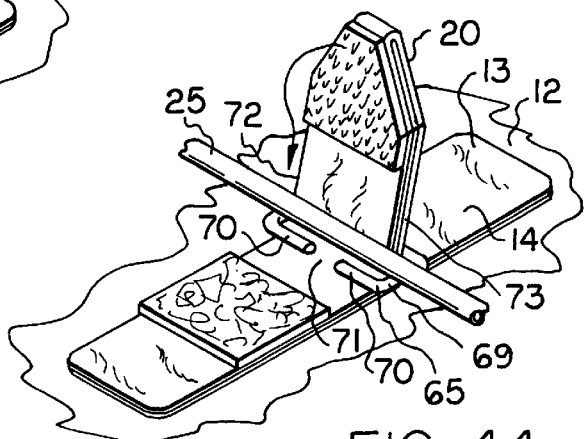
FIG. 44 is a fragmentary perspective view of the catheter securing assembly mounted on a surface with a catheter positioned relative thereto for securement therewith.
Figure 45:
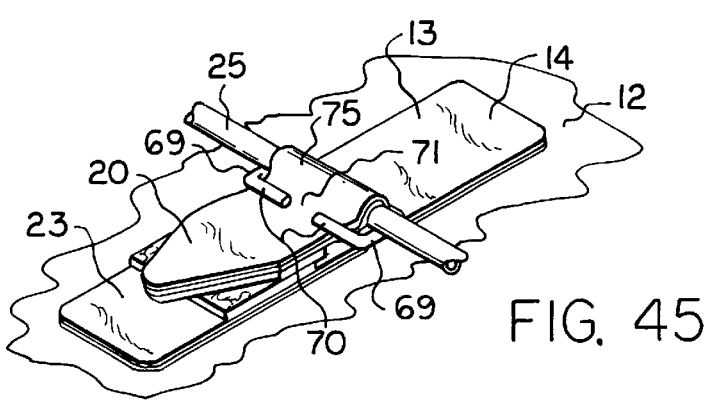
FIG. 45 is a fragmentary perspective view of the catheter finally secured to the catheter securing assembly.

In FIGS. 43–45 another embodiment of a securing tape assembly is shown. FIG. 43 is very similar to FIG. 37 except that the loop member 65 is shown in a reverse position, as can be seen from a comparison of FIG. 43 with FIG. 37. More specifically, the loop ends 70 of loop member 65 are located on the side of tab 20 which carries the hook member 21 whereas in the embodiment of FIG. 37, the elongated side 67 of the loop member 65 was on the side of tab 20 which carried hook member 21.

In order to secure the catheter 25 to the securing tape assembly of FIG. 44, it is laid across the loop portions 69 of loop member 65. Thereafter, the tab 20 is threaded through opening 71 between loop ends 70 as described above relative to FIGS. 40 and 41. In this respect, one side 73 of tab 19 is threaded through opening 71 and thereafter the opposite side 72 of tab 20 is threaded through opening 71, and thereafter, the tab 20 is pulled taut and the tab 20 is attached to tape portion 23 to thereby cause the loop portions 69 to press on one side of tube 25 and the portion 75 of the tape to press on the opposite side of tube 25, to thereby firmly secure catheter 25 to the securing tape assembly shown in FIG. 45. FIGS. 43–45 are a condensation of the step shown in FIGS. 39–42, but the procedure of securing the catheter is analogous to the steps discussed above relative to FIGS. 39–42.

Figure 46:
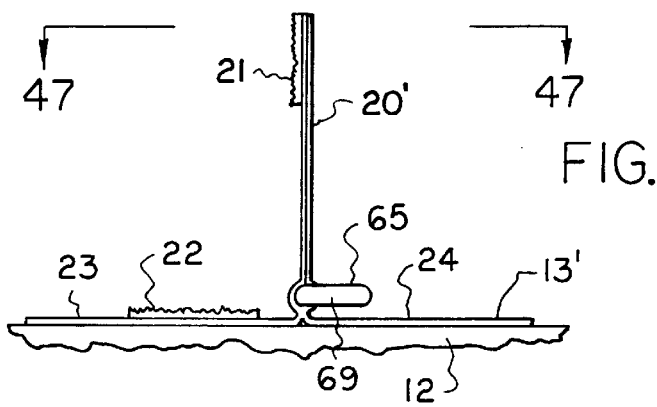
FIG. 46 is a schematic side elevational view similar to FIG. 21 but showing the loop member of FIG. 36 secured to the tab.
Figure 47:
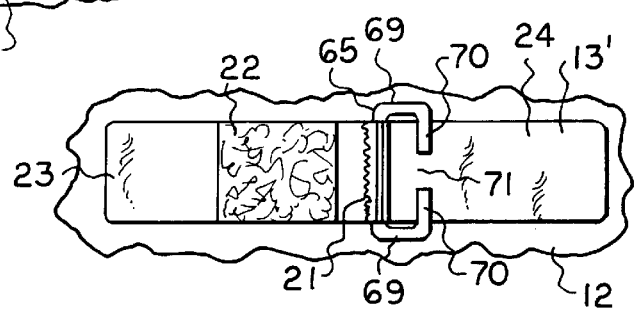
FIG. 47 is a fragmentary plan view taken substantially in the direction of arrows 47—47 of FIG. 46.

In FIGS. 46–50 another embodiment of the present invention is disclosed. FIG. 46 is similar to FIG. 21 and identical numerals will be used where applicable. In this respect, the securing tape 13' includes ends 23 and 24 which are identical to the ends of the securing tape shown in FIG. 21. The tab 20' is identical to tab 20' of FIG. 21. The loop member 65 is captured between the sides of tab 20'. As noted above relative to FIGS. 21–24, the tab 20' is formed of two sides of an elongated tape which are placed with their adhering surfaces in face-to-face relationship and adhered to each other. The portion 67 (FIG. 36) of loop member 65 is captured between these two sides as depicted in FIG. 46.

Figure 48:
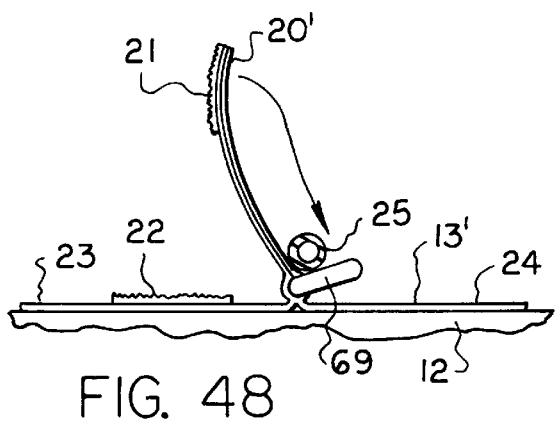
FIG. 48 is a fragmentary side elevational view partially in cross section showing the first step of securing a catheter to the securing tape assembly.
Figure 49:
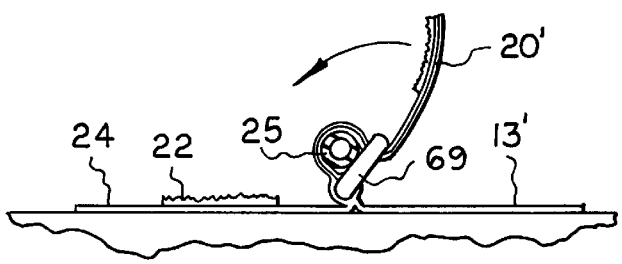
FIG. 49 is a fragmentary side elevational view partially in cross section showing the next step of securing the catheter to the securing tape assembly.

The catheter 25 is secured to the securing tape assembly by initially placing it in the position of FIG. 48 wherein it lies across loop portions 69. Thereafter, the tab 20' is threaded through the opening 71 between loop ends 70, as described above, so that it assumes the position of FIG. 49. Thereafter, tab 20' is pulled taut and the hook fabric 21 is secured to the pile fabric 22 so that the catheter 25 is firmly secured as shown in FIG. 50 with the loop portions 69 bearing on one side of catheter 25 and the tab 20' bearing on the opposite side of catheter 25.

In FIGS. 51–54 a further embodiment of the present invention is disclosed. In this embodiment the loop member 65 is oriented in an exactly opposite manner than shown in FIG. 46. However, all other parts of the tape 13' are identical to the tape of FIG. 46.

In order to secure a catheter 25 to securing tape 13' which is mounted on a body 12, the catheter 25 is laid across loop portions 69 (FIG. 53), and thereafter the tab 20' is passed around catheter 25 and through the opening 71 between loop member ends 70 as described above so that it occupies a position under loop ends 70. Thereafter, tab 20' is pulled taut and the hook member 21 is secured to the pile member 22 to thereby firmly secure the catheter in position.

Figure 50:
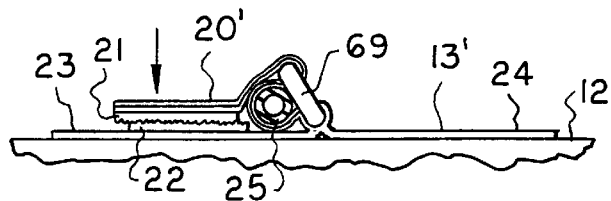
FIG. 50 is a fragmentary side elevational view partially in cross section showing the catheter secured to the securing tape assembly.
Figure 51:
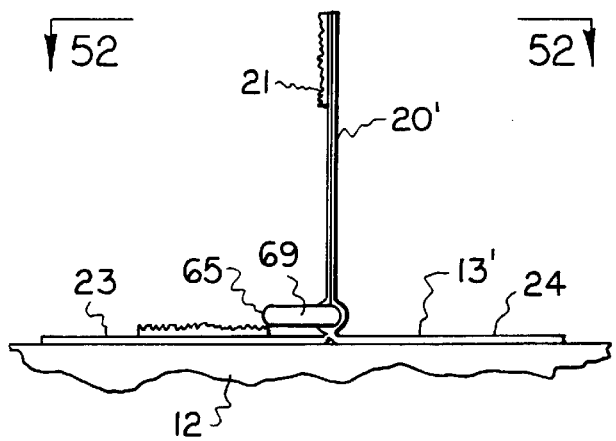
FIG. 51 is a schematic view similar to FIG. 46 but showing the loop member positioned on the opposite side of the tape than shown in FIG. 46.
Figure 52:
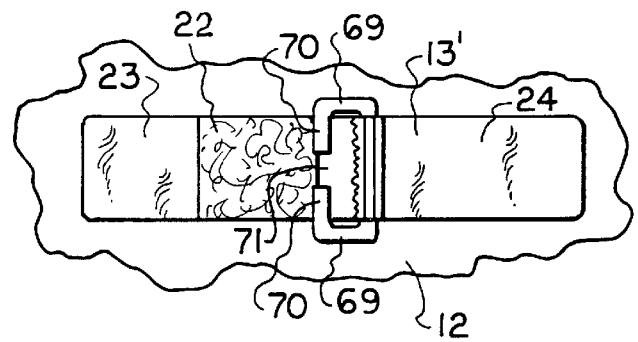
FIG. 52 is a fragmentary plan view taken substantially in the direction of arrows 52—52 of FIG. 51.
Figure 53:
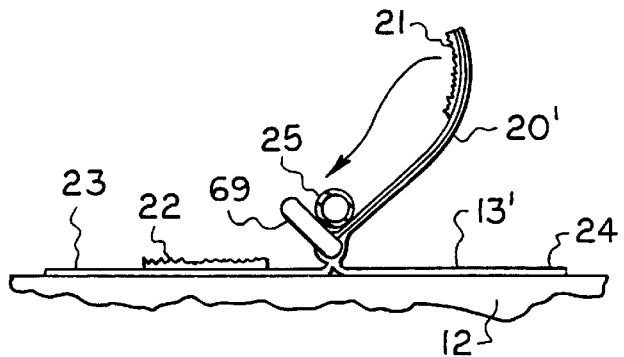
FIG. 53 is a fragmentary side elevational view partially in cross section similar to FIG. 49 and showing the next step of securing a catheter to the securing tape assembly.
Figure 54:
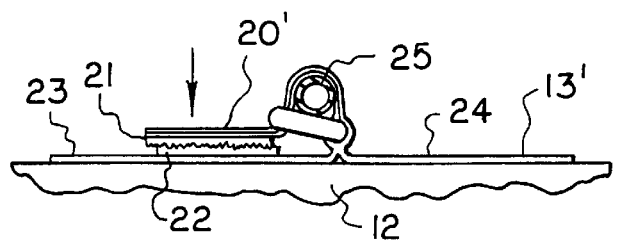
FIG. 54 is a fragmentary side elevational view partially in cross section similar to FIG. 50 and showing the catheter secured to the securing tape assembly.

A comparison of FIGS. 54 and 50 shows the difference between the embodiment of FIGS. 46–50 and the embodiment of FIGS. 51–54. In the embodiment of FIGS. 46–50 the loop portions 69 bear on the top of catheter 25 and the tab 20' bears on the opposite side of catheter 25. Therefore the complete assembly has the appearance of FIG. 42 wherein the portion of the catheter 25 between loop portions 69 is visible. However, in the embodiment of FIGS. 51–54 the final assembly of FIG. 54 has the same appearance as that shown in FIG. 45 wherein the central portion of catheter 25 between loop portions 69 is covered by the tab 20'.

The loop member 65 (FIG. 36) can also be positioned in the same manner as described above for the D-ring of FIG. 21A, that is, below the securing tape at the junction of the tape ends.

As can be seen from the above description, the securing tape or band can be used with a loop member which can be a closed loop member, such as an O-ring or the members shown in FIGS. 12–15 or modifications thereof, or with an open loop member 65, such as shown in FIG. 36, or modifications of the latter which have spaced loop portions which engage a catheter and loop ends and a space between the loop ends through which a tab can be passed.

It will be appreciated that in all the embodiments disclosed heretofore when the loop member and the tab tightly engage the catheter, the latter can be firmly secured regardless of the material of the loop member. In other words, there need not be a silicone-to-silicone engagement between the loop member and a silicone catheter in order for there to be tight engagement. However, a silicone-to-silicone engagement is preferred when a silicone catheter is being secured. Therefore, it will be appreciated that the loop member 65 can be coated with silicone rubber if desired. Conversely, if desired, the loop member, whether it is an O-ring or a loop member, such as 65, can have a coating of adhesive for providing an adhesive engagement in addition to the tight engagement which would otherwise be produced when a tab, such as 20, is pulled taut and placed into engagement with the base, as described above. Also, if desired, the loop members can be coated with an abrasive material or open cell sponge for the purpose of increasing the gripping power of the loop member.

While a great part of the specification has been directed to the combination of a silicone rubber loop securing a silicone rubber catheter to a securing tape assembly, it will be appreciated that a loop of other materials, such as plastic or non-silicone rubber or any flexible material, can be used to secure a silicone rubber tube or a non-silicone rubber tube to a base because of the combination of the frictional engagement between the tab and the tube and because of the frictional engagement between the loop member and the tube. The silicone rubber O-rings which were referred to previously are manufactured by or for Apple Rubber Products, Inc. of Lancaster, N.Y. and identified by number AS568A-111. It will be appreciated that various durometers may be used.

It is to be noted that in all embodiments of the present application there are two circumferentially spaced portions of a loop which engage two spaced portions along the longitudinal extent of a tab and that there are two other circumferentially spaced portions of the loop between the first circumferentially spaced portions which engage longitudinally spaced portions of a tube proximate the edges of the tab. It is by this interengaging relationship that the tube is firmly secured to a tab. The foregoing interengaging relationship can be clearly seen, for example, from FIGS. 6, 40, 42 and 45.

While preferred embodiments of the present invention have been disclosed, it will be appreciated that it is not limited thereto but may be otherwise embodied within the scope of the following claims.

What is claimed is:

1. A securing tape assembly comprising a tape, first and second surfaces on said tape, pressure-sensitive adhesive on said first surface, a tab extending outwardly relative to said second surface, said tab having an end attached to said tape and having a free end, a first attachment member on said tab remote from said attached end, a second attachment member on said second surface engageable by said first attachment member, and a loop member which is a different member than said tab positioned relative to said tab.

2. A securing tape assembly as set forth in claim 1 wherein said loop member is secured relative to said tab.

3. A securing tape assembly as set forth in claim 1 wherein said first attachment member is one of hook fabric or pile fabric, and the second attachment member is the other of hook fabric or pile fabric.

4. A securing tape assembly as set forth in claim 1 wherein said loop member is an O-ring fabricated from silicone rubber.

5. A securing tape assembly as set forth in claim 1 wherein said loop member is a closed loop member.

6. A securing tape assembly as set forth in claim 5 wherein said closed loop member is an O-ring.

7. A securing tape assembly as set forth in claim 1 wherein said loop member is an open loop member.

8. A securing tape assembly as set forth in claim 7 wherein said open loop member is in the form of a C.

9. A securing tape assembly comprising a tape having an inner surface and a nonadhesive outer surface, outer end portions on said tape for mounting on a foreign body, pressure-sensitive adhesive on said inner surface of said outer end portions, a central tab portion on said tape having an end attached to said tape and a free end, said central tab portion being positioned between said outer end portions for engaging the circumferential portion of a tube, and a loop member which is a different member than said tab for engaging said central portion and pressing said central portion of said tape against said circumferential portion of a tube.

10. A securing tape assembly as set forth in claim 9 wherein said loop member includes spaced portions engaging said tube at spaced locations.

11. A securing tape assembly as set forth in claim 10 wherein said loop member is fabricated of silicone rubber.

12. A securing tape assembly as set forth in claim 9 wherein said loop member is a closed loop member.

13. A securing tape assembly as set forth in claim 9 wherein said loop member is an open loop member.

14. A securing tape assembly and tube combination comprising a tube and a tape having an inner surface and a nonadhesive outer surface, outer end portions on said tape for mounting on a foreign body, pressure-sensitive adhesive on said inner surface of said outer end portions, a tab portion on said tape having an end attached to said tape and a free end, said tab for engaging the circumferential portion of said tube, and a loop member which is a different member than said tab for engaging said tab portion of said tape and pressing said tab portion of said tape against a circumferential portion of said tube.

15. A securing tape assembly as set forth in claim 14 wherein said loop member includes portions engaging said tube at spaced locations.

16. A securing tape assembly as set forth in claim 15 wherein said loop member is fabricated of silicone rubber.

17. A securing tape assembly as set forth in claim 14 wherein said loop member is a closed loop member.

18. A securing tape assembly as set forth in claim 14 wherein said loop member is an open loop member.

19. A securing assembly and tube combination comprising a tube, and a securing assembly comprising a base, a tab having an end secured to said base and a free end, and a loop member which is a different member than said tab securing said tube to said tab.

20. A securing assembly and tube combination as set forth in claim 19 wherein said base comprises a tape having first and second surfaces, adhesive on said first surface, a first attachment member on said base, and a second attachment member on said tab wherein said first attachment member is one of hook fabric or pile fabric, and the second attachment member is the other of hook fabric or pile fabric.

21. A securing assembly and tube combination as set forth in claim 19 including a first attachment member on said base, and a second attachment member on said tab.

22. A securing assembly and tube combination as set forth in claim 21 wherein said first attachment member is one of hook fabric or pile fabric, and the second attachment member is the other of hook fabric or pile fabric.

23. A securing assembly and tube combination as set forth in claim 21 wherein said tube and said loop member are both fabricated from silicone rubber.

24. A securing assembly and tube combination as set forth in claim 19 including an adhesive surface on said tab.

25. A securing assembly and tube combination as set forth in claim 19 wherein said base comprises a band.

26. A securing assembly and tube combination as set forth in claim 25 wherein said tab is connected to said band.

27. A securing assembly and tube combination as set forth in claim 19 wherein said loop member is a closed loop member.

28. A securing assembly and tube combination as set forth in claim 19 wherein said loop member is an open loop member.

29. A securing assembly comprising a base member, a tab having an end secured to said base member and a free end, and a loop member associated with said tab, said loop member being a different member than said tab.

30. A securing assembly as set forth in claim 29 wherein said loop member is a closed loop member.

31. A securing assembly as set forth in claim 29 wherein said loop member is an open loop member.

32. A securing assembly as set forth in claim 29 wherein said base member is a tape having an adhesive surface.

33. A securing assembly as set forth in claim 32 including a first attachment member on said tape, and a second attachment member on said tab.

34. A securing assembly as set forth in claim 33 wherein said loop member is a closed loop member.

35. A securing assembly as set forth in claim 33 wherein said loop member is an open loop member.

36. A securing assembly as set forth in claim 29 wherein said loop member is secured relative to said tab.

37. A securing assembly as set forth in claim 36 wherein said loop member is a closed loop member.

38. A securing assembly as set forth in claim 37 wherein said loop member is an open loop member.

39. A securing assembly as set forth in claim 36 including a first attachment member on said base member, and a second attachment member on said tab.

40. A securing assembly as set forth in claim 39 wherein said loop member is a closed loop member.

41. A securing assembly as set forth in claim 39 wherein said loop member is an open loop member.

42. A securing assembly as set forth in claim 29 wherein said base member is a band.

43. A securing assembly as set forth in claim 42 including a first attachment member on said band, and a second attachment member on said tab.

44. A securing assembly as set forth in claim 43 wherein said loop member is a closed loop member.

45. A securing assembly as set forth in claim 40 wherein said loop member is an open loop member.

46. A securing tape assembly comprising a tape, first and second surfaces on said tape, pressure-sensitive adhesive on said first surface, a tab extending outwardly relative to said second surface, a first attachment member on said tab, a second attachment member on said second surface, and a loop member having circumferentially spaced loop portions positioned relative to said tab for engagement with spaced portions of said tab.

47. A securing tape assembly comprising a tape having a inner surface and a nonadhesive outer surface, outer end portions on said tape for mounting on a foreign body, pressure-sensitive adhesive on said inner surface of said outer end portions, a central portion on said tape between said outer end portions for engaging the circumferential portion of a tube, and a loop member having circumferentially spaced loop portions for engaging spaced portions of said central portion of said tape and pressing said central portion of said tape against said circumferential portion of a tube.

48. A securing tape assembly as set forth in claim 47 wherein said tab has outer edges, and second circumferentially spaced loop portions for engaging said tube proximate said outer edges.

49. A securing tape assembly and tube combination comprising a tube and a tape having an inner surface and a nonadhesive outer surface, outer end portions on said tape for mounting on a foreign body, pressure-sensitive adhesive on said inner surface of said outer end portions, a portion on said tape for engaging the circumferential portion of said tube, and a loop member having circumferentially spaced loop portions for engaging spaced portions of said portion of said tape and pressing a portion of said tape between said spaced portions of said tape against a circumferential portion of said tube.

50. A securing tape assembly and tube combination as set forth in claim 49 wherein said portion on said tape for engaging the circumferential portion of said tube has outer edges, and second circumferentially spaced loop portions for engaging said tube proximate said outer edges.

51. A securing assembly and tube combination comprising a tube, and a securing assembly comprising a base, a tab secured to said base, and a loop member having circumferentially spaced loop portions securing spaced portions of said tab therebetween to said tube.

52. A securing assembly and tube combination as set forth in claim 51 wherein said portion of said tab between said circumferentially spaced loop portions has outer edges, and second circumferentially spaced loop portions between said loop portions engaging said tube proximate said outer edges of said tab.

53. A securing assembly and tube combination as set forth in claim 52 wherein said loop member is an open loop member, and wherein said tab has an end attached to said base member and a free end, and wherein said open loop member has a closed portion and an open portion, and wherein said open portion is positioned between said closed portion and said free end of said tab.

54. A securing assembly comprising a base member, a tab having a longitudinal extent on said base member, and a loop member having circumferentially spaced loop portions for engaging spaced locations along said longitudinal extent of said tab with a portion of said tab between said circumferentially spaced loop portions.

55. A securing tape assembly as set forth in claim 54 wherein said portion of said tab between said circumferentially spaced loop portions has outer edges, and second circumferentially spaced loop portions for engaging a tube proximate said outer edges.

56. A securing assembly as set forth in claim 55 wherein said loop member is an open loop member.

57. A securing assembly as set forth in claim 56 wherein said tab has an end attached to said base member and a free end, and wherein said open loop member has a closed portion and an open portion, and wherein said open portion is positioned between said closed portion and said free end of said tab.

* * * * *

UNITED STATES PATENT AND TRADEMARK OFFICE
CERTIFICATE OF CORRECTION

PATENT NO. : 6,565,537 B2
DATED : May 20, 2003
INVENTOR(S) : Dennis R. Tollini

It is certified that error appears in the above-identified patent and that said Letters Patent is hereby corrected as shown below:

Column 13,
Line 21, change "40" to -- 43 --.

Column 14,
Line 41, change "55" to -- 54 --.

Signed and Sealed this

Ninth Day of September, 2003

JAMES E. ROGAN
*Director of the United States Patent and Trademark Office*